United States Patent
Kaiser et al.

(10) Patent No.: US 9,480,824 B2
(45) Date of Patent: Nov. 1, 2016

(54) CUFF-RESISTANT ANCHORING BALLOON FOR MEDICAL DEVICE

(71) Applicant: HOLOGIC, INC., Marlborough, MA (US)

(72) Inventors: Christopher Charles Kaiser, Holliston, MA (US); Jessica Tina Schenck, Shrewsbury, MA (US)

(73) Assignee: Hologic, Inc., Bedford, MA (US)

( * ) Notice: Subject to any disclaimer, the term of this patent is extended or adjusted under 35 U.S.C. 154(b) by 314 days.

(21) Appl. No.: 14/139,609

(22) Filed: Dec. 23, 2013

(65) Prior Publication Data
US 2015/0174380 A1  Jun. 25, 2015

(51) Int. Cl.
*A61M 29/00* (2006.01)
*A61M 25/10* (2013.01)
(Continued)

(52) U.S. Cl.
CPC ..... *A61M 25/1002* (2013.01); *A61M 25/0017* (2013.01); *A61M 25/04* (2013.01); *A61M 25/1027* (2013.01); *A61M 25/1029* (2013.01); *A61B 2018/00279* (2013.01); *A61B 2018/00285* (2013.01); *A61M 25/1006* (2013.01); *A61M 25/1011* (2013.01); *A61M 25/1025* (2013.01); *A61M 25/1034* (2013.01); *A61M 25/1036* (2013.01); *A61M 2025/1043* (2013.01);
(Continued)

(58) Field of Classification Search
CPC ............... A61B 2018/00285; A61M 25/1002; A61M 25/1004; A61M 25/1006; A61M 25/1011; A61M 25/1017; A61M 25/1025; A61M 25/1027; A61M 25/1029; A61M 25/1034; A61M 25/1036; A61M 2025/1043; A61M 2025/1059; A61M 2025/1068
See application file for complete search history.

(56) References Cited

U.S. PATENT DOCUMENTS 5,707,357 A   1/1998   Mikail et al.
5,827,225 A   10/1998  Ma Schwab
(Continued)

FOREIGN PATENT DOCUMENTS

EP   0421031 B1   6/1993
WO   89/11306     11/1989
(Continued)

OTHER PUBLICATIONS

PCT International Search Report and Written Opinion for International Application No. PCT/US2014/063885, Applicant Hologic, Inc., forms PCT/ISA/210, 220, and 237, dated Mar. 13, 2015 (13 pages).

*Primary Examiner* — Robert Lynch
(74) *Attorney, Agent, or Firm* — Vista IP Law Group, LLP (57) ABSTRACT

A medical device having an elongate support structure and an inflatable balloon including a first-end portion secured to the support structure at a first location, a second-end portion secured to the support structure at a second location distal to the first location, and a middle-body portion. The first-end portion has a wall thickness greater than a wall thickness of the middle-body portion; the balloon defines a sealed interior through which the support structure extends. The balloon being stretch-mounted to the support structure in tension relative to the support structure; the balloon is formed in a diamond-like configuration that transitions to a substantially spherical configuration when the balloon is inflated to a inflation pressure that is at least about ten percent greater than atmospheric pressure, such that when inflated to the inflation pressure and anchored in an anatomical body region, resists movement of the support structure relative to the balloon.

18 Claims, 7 Drawing Sheets

(51) Int. Cl.
　　　*A61M 25/00*　　　(2006.01)
　　　*A61M 25/04*　　　(2006.01)
　　　*A61B 18/00*　　　(2006.01)

(52) U.S. Cl.
　　　CPC ............... *A61M2025/1059* (2013.01); *A61M 2025/1061* (2013.01); *A61M 2025/1068* (2013.01)

(56) References Cited

U.S. PATENT DOCUMENTS

| | | | |
|---|---|---|---|
| 5,853,389 A * | 12/1998 | Hijlkema | A61M 25/1002 604/103.07 |
| 6,796,972 B1 | 9/2004 | Sinofsky et al. | |
| 8,070,717 B2 | 12/2011 | Goebel | |
| 8,454,648 B1 | 6/2013 | Isham | |
| 2003/0009079 A1 | 1/2003 | Beaufore et al. | |
| 2004/0199086 A1 | 10/2004 | Crisp | |
| 2005/0288630 A1 * | 12/2005 | Conway | A61M 25/0017 604/96.01 |
| 2012/0109179 A1 * | 5/2012 | Murphy | A61F 2/01 606/194 |
| 2012/0239046 A1 * | 9/2012 | Kaiser | A61B 17/025 606/90 |
| 2014/0074020 A1 * | 3/2014 | Wantink | A61M 25/001 604/96.01 |

FOREIGN PATENT DOCUMENTS

| | | |
|---|---|---|
| WO | 98/39044 | 9/1998 |
| WO | 2007/005239 | 1/2007 |
| WO | 2013/040522 | 3/2013 |

* cited by examiner

| | INFLATED WITH 2CC OF FLUID | INFLATED WITH 3CC OF FLUID | INFLATED WITH 4CC OF FLUID | INFLATED WITH 5CC OF FLUID | INFLATED WITH 6CC OF FLUID |
|---|---|---|---|---|---|
| DISCLOSED ANCHORING BALLOON 120 (FIG. 3A-4, 6A) | 5 PSI | 8.5 PSI | 11 PSI | 11 PSI | 12 PSI |
| SIZE OF DISCLOSED ANCHORING BALLOON 120 (FIGS. 3A-4, 6A) | LENGTH: .795" DIAMETER: .610" | LENGTH: .810" DIAMETER: .717" | LENGTH: .830" DIAMETER: .782" | LENGTH: .850" DIAMETER: .860" | LENGTH: .860" DIAMETER: .895" |
| Universa® Silicon Foley Catheter 12 French by Cook Medical | 6 PSI | 6 PSI | 6 PSI | 6 PSI | 6 PSI |
| Size of Universa® | LENGTH: .505" DIAMETER: .646" | LENGTH: .548" DIAMETER: .732" | LENGTH: .615" DIAMETER: .795" | LENGTH: .673" DIAMETER: .867" | LENGTH: .718" DIAMETER: .890" |

*FIG. 6B*

| TEST SPECIMEN | LOCATION OF .2LBF | LOCATION OF .5LBF | SLOPE |
|---|---|---|---|
| Universa® Silicon Foley Catheter 12 French by Cook Medical | 0.000" | .259" | 1.16 |
| DISCLOSED ANCHORING BALLOON 120 (FIG. 3A-4, 6A) | 0.000" | .061" | 4.92 |

*FIG. 7*

CUFF-RESISTANT ANCHORING BALLOON FOR MEDICAL DEVICE

FIELD OF THE INVENTION

The present disclosure relates generally to medical devices and methods of manufacturing such devices. More particularly, the present disclosure relates to anchoring devices for elongated tubular members, such as catheters and probes.

BACKGROUND

The use of medical catheters and probes has become an effective method for treating many types of diseases. In general, a suitable catheter or tubular probe is inserted into a body lumen of the patient (vascular or non-vascular) and navigated through the body lumen into a desired target site. Using this method, virtually any target site in the patient's body may be accessed. In certain treatments, it is desirable to secure the catheter or probe in some manner so that proper positioning and placement is maintained during the treatment, such as in some urinary incontinence treatments.

Urinary incontinence is one of the most prevalent conditions of the lower urinary tract, particularly, stress urinary incontinence (hereinafter SUI) which affect a significant amount of people. SUI is the loss of small amounts of urine associated with movements, such as coughing, sneezing, laughing, and exercise that cause increased pressure on the bladder based on increased intra-abdominal pressure. Some SUI treatment includes the delivery of energy to and/or through the urethral wall by precisely placing an elongated probe having an energy delivery element within the urinary tract. These probes usually have an anchoring member, such as an inflatable balloon, at a distal portion of the probe that sits in a patient's bladder, and a locking device at the proximal portion of the probe that is placed against the patient's external urethral orifice or urinary meatus, thereby securing the probe and the energy delivery member in a desirable position within the urethra. During these treatments, minimizing movement of the probe relative to the desired treatment site in the urethra and/or paraurethral region is desirable.

In the past, various devices have been used for securing the positioning a catheter or probe relative to a treatment site, such as urologic bladder balloons. While known bladder balloons may hold indwelling catheters (e.g. Foley-type) from "falling out" of a bladder over a period of time by readily adapting to the bladder and body structures, and further preventing urine leakage, these balloons also allow axial displacement of the catheter relative to the balloon (i.e. cuffing) and a relative large range of axial displacement of the catheter within the urethra. Cuffing refers to the balloon tendency to fold over on itself or shift toward the bladder end of an indwelling catheter. The application of axial force to the indwelling catheter may cause cuffing and deformation of the bladder balloon and further causes axial movement of the catheter within the urethra, even when the balloon still sits within the bladder preventing expulsion from the patient. Thus, these known bladder balloons do not resist axial movement of the catheter relative to the balloon or relative to a desirable treatment site within the urthera and/or paraurethral region. Further, the known conforming urologic bladder balloons do not provide a prompt and sharp tactile feedback to the user or physician when the balloon reaches or locates the bladder neck, particularly when low force is applied to the balloon. Because these balloons are conforming and readily adaptable to body structures, the feedback is usually difficult to notice when low force is applied.

Accordingly, there is an ongoing need to provide for a more suitable anchoring balloon that minimizes axial translation of a catheter or probe, when the catheter or probe is positioned at a desired treatment site and axial force is applied to the catheter or probe. Further, there is an ongoing need for a more suitable anchoring balloon that resists cuffing of the balloon or axial displacement of the catheter or probe relative to the balloon. Additionally, there is an ongoing need for a more suitable anchoring balloon that provides a prompt and sharp rise in tactile feedback to the user or physician that signals the location of the balloon within a body structure or cavity when low force is applied.

SUMMARY

In one embodiment of the disclosed inventions, a medical device, having an elongate support structure and an inflatable balloon is described. The inflatable balloon includes a first-end portion secured to the support structure at a first location, a second-end portion secured to the support structure at a second location distal to the first location, and a middle-body portion. The middle-body portion of the balloon has a first end integrally formed with or otherwise bonded to the first-end portion, and a second end integrally formed with or otherwise bonded to the second-end portion. The first-end portion has a wall thickness greater than a wall thickness of the middle-body portion; the respective first-end portion, middle-body portion and second-end portion collectively define a sealed interior of the balloon through which the support structure extends. The balloon being stretch-mounted to the support structure so as to be in tension relative to the support structure, wherein the balloon is formed in a diamond-like configuration that transitions to a substantially spherical configuration when the balloon is inflated to a inflation pressure that is at least about ten percent greater than atmospheric pressure external to the balloon, such that the balloon, when inflated to the inflation pressure and anchored in an anatomical body region, resists movement of the support structure relative to the balloon.

By way of non-limiting example, the balloon middle-body portion is twisted relative to the support structure. The support structure includes a plurality of elongate members, and wherein the first-end portion of the balloon is secured to a first elongate member of the support structure, and the second-end portion of the balloon is secured to a second elongate member of the support structure. The first-end portion and second-end portion of the balloon are each secured to the support structure by one of adhesive bonding, thermal bonding, interlocking geometries, and mechanical fastening. The balloon comprises one or more polymeric materials.

In various embodiments of the disclosed inventions, the balloon has a shore durometer in a range of between about A90 to about A100. The balloon has a shore durometer in a range of between about D30 to about D70. The balloon, when inflated to the inflation pressure, resists cuffing relative to the support structure. The second inflation pressure is at least about 10 percent greater than the first inflation pressure.

In accordance with embodiments of the disclosed inventions, the balloon middle-body portion has a non-tensioned length, and wherein the balloon middle-body portion is stretched to a tensioned length that is in a range of about 8% to about 12% greater than the non-tensioned length.

In accordance with another embodiment of the disclosed inventions, a method of manufacturing a medical device, includes forming an inflatable balloon having a first-end portion, a second-end portion, and a middle-body portion, the middle-body portion having a first end integrally formed with or otherwise bonded to the first-end portion, and a second end integrally formed with or otherwise bonded to the second-end portion, the first-end portion having a wall thickness greater than a wall thickness of the middle-body portion; securing the first-end portion of the balloon to a first location on an elongate support structure; and securing the second-end portion of the balloon to a second location distal to the first location on the elongate support structure, the first and second locations being spaced apart such that the balloon is stretch-mounted to the support structure so as to be in tension relative to the support structure, the first-end portion, middle-body portion and second-end portion of the balloon collectively define a sealed interior of the balloon through which the support structure extends, wherein the balloon is formed in a diamond-like configuration that transitions to a substantially spherical configuration when the balloon is inflated to a inflation pressure that is at least about ten percent greater than atmospheric pressure external to the balloon.

By way of non-limiting example, the middle-body portion of the balloon is twisted relative to the support structure prior to securing the second-end portion of the balloon to the support structure. The support structure includes a plurality of elongate members, and wherein the first-end portion of the balloon is secured to a first elongate member of the support structure, and the second-end portion of the balloon is secured to a second elongate member of the support structure. The first-end portion and second-end portion of the balloon are each secured to the support structure by one of adhesive bonding, thermal bonding, interlocking geometries, and mechanical fastening. The balloon comprises one or more polymeric materials.

In various embodiments of the disclosed inventions, the balloon includes a shore durometer in a range of between about A90 to about A100. The balloon includes a shore durometer in a range of between about D30 to about D70. The balloon middle-body portion has a non-tensioned length, and wherein the balloon middle-body portion is stretched to a tensioned length that is in a range of about 8% to about 12% greater than the non-tensioned length.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. The relative scale of select elements may have been exaggerated for clarity. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION OF THE ILLUSTRATED EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the inventions or as a limitation on the scope of the inventions, which are defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

Figure 1:
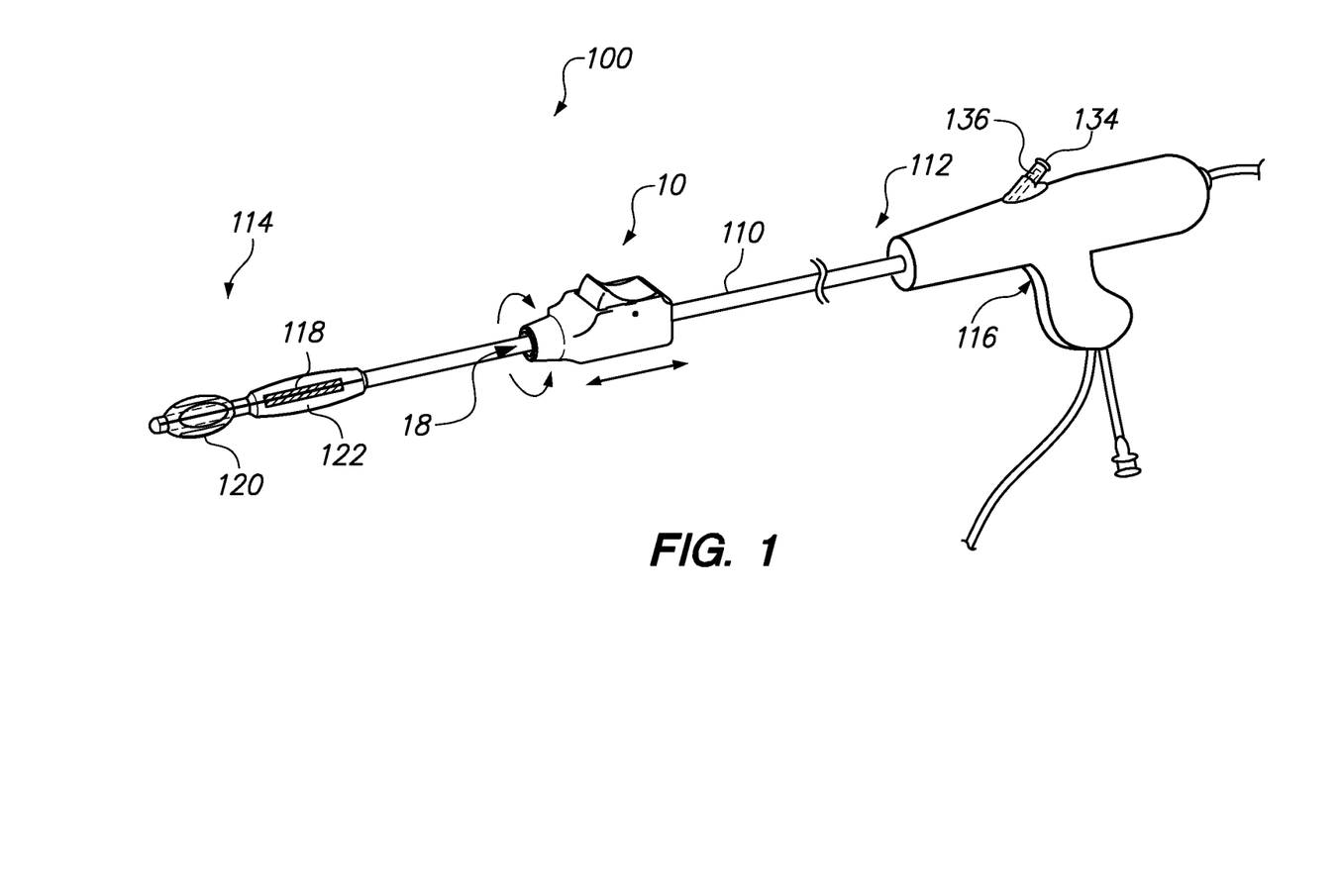
FIG. 1 is a plan view of a SUI assembly constructed according to one embodiment of the disclosed inventions.

FIG. 1 illustrates a SUI assembly 100 according to the disclosed inventions. The SUI assembly 100 includes an elongate member 110 having a proximal portion 112, a distal portion 114, and defining one or more inner lumens extending therebetween (shown in FIG. 4). The proximal portion 112 of the elongate member 110 is coupled to a handle 116. The distal portion 114 of the elongate member 110 includes an anchoring balloon 120, a cooling balloon 122 and an energy delivery member 118 (e.g. transducer) disposed within the cooling balloon 122. The one or more lumens of the elongate member 110 are in fluid communication with respective anchoring 120 and cooling 122 balloons for inflation and/or deflation of the balloons with fluid and/or gas. The SUI assembly may be made of polymeric materials and/or alloy materials, such as polyethylene, stainless steel or other suitable biocompatible materials or combinations thereof. As used in this specification, the term "elongate member" may refer to any member having a variety of elongated shapes, including a catheter, a tubular probe, a shaft, a needle, a wire, a sleeve, or any other configuration.

Figure 2:
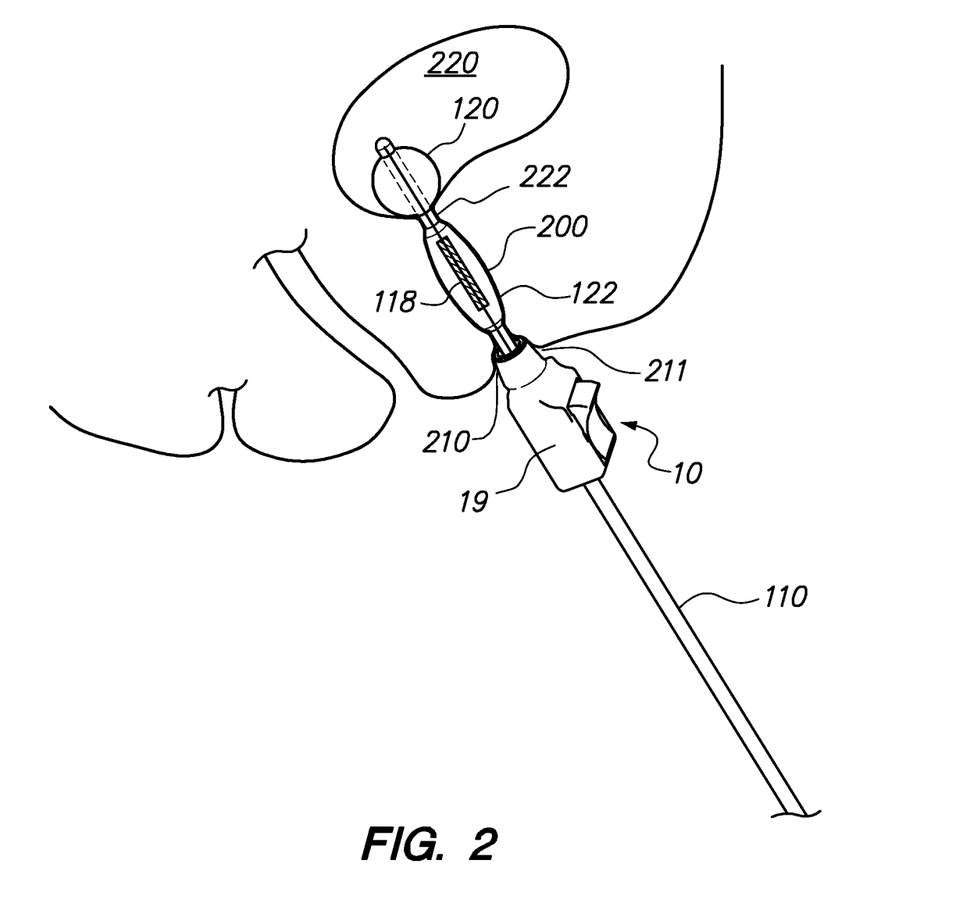
FIG. 2 is a cross-sectional view of an exemplary method of use of the SUI assembly of FIG. 1.

The SUI assembly 100 further includes an adjustable locking device 10 disposed around the elongate member 110. The adjustable locking device 10 includes a housing 19 and an axial elongate passageway 18 for allowing passage of the elongate member 110 (FIGS. 1-2). For example, the passageway 18 may have a diameter larger than the outer diameter of the elongate member 110, when the locking device 10 is disengaged, so that, the locking device 10 slides over and/or rotates around the elongate member 110 with minimal friction or non-friction to the elongate member 110. As used in this specification, the term "engaged" may refer to the adjustable locking device 10 being activated, actuated or in a locked position along the length of the elongate member 110, and the term "disengaged" may refer to the locking device 10 being deactivated, in an unlocked position, freely movable along the length of the elongate member 110.

FIG. 2 illustrates an exemplary method of use of the assembly 100 of FIG. 1 for treatment of SUI in a female patient. After gaining access to a patient's urethra 200, the elongate member 110 is introduced until the anchoring balloon 120 is disposed within a bladder 220. Then, the anchoring balloon 120 is inflated and positioned at the neck 222 of the bladder 220, where the anchoring balloon 120 sits against the orifice of the interior of the bladder so that the energy delivery member 118, disposed within the cooling balloon 122, in positioned in the urethra 200 at a desired treatment site. An advantage of the disclosed inventions is that the target force for the SUI assembly 100 having the anchoring balloon 120 (further disclosed in FIGS. 3A-4, 6A) is approximately 0.5 pound force (lbf) when the user or physician pulls back (i.e. withdraw motion) on the handle 116 and/or the elongate member 110 coupled to the anchoring balloon 12, so that the user or physician detects contact and/or seating of the balloon 120 with the bladder neck 222 via tactile feedback (FIG. 7). When using the anchoring balloon 120, the force to detect contact and/or seating with a body cavity is relatively low (e.g. approximately 0.5 lbf). Another advantage of the low applied force when positioning the anchoring balloon 120 within the bladder 220 and pulling to detect its seating against the neck 222 is to minimize or avoid deformation of the urethra 200, so that the energy delivery element 118 is disposed in the desired position, and the anatomy and length of the urethra 200 is maintained. For example, if a higher force (approximately 2 lbf) is required to detect contact/seating of a balloon at the bladder neck 222, the higher force will compress or deform the anatomy and/or length of the urethra 220, which may result in misplacement of an energy delivery element.

Further advantage of the disclosed inventions is that the anchoring balloon 120 resists axial movement of the elongate member 110 relative to the anchoring balloon 120, which will be discussed in greater detail below. When the elongate member 110 is axially moved, the anchoring balloon 120 moves axially as well, so that cuffing is not produced or at least minimized at the anchoring balloon 120 when the elongated member 110 moves. The adjustable locking device 10 is then advanced or distally moved along the elongate member 110 to press against the external urethral orifice, urinary meatus 210 and/or adjacent tissue 211, and engages the elongate member 110 to thereby secure the elongate member 110 at the desired position. It will be appreciated that placement of the anchoring balloon 120 within the bladder 220 (e.g. seating at the neck 222) and engagement of the locking device 10 to the elongate member 110, provides a controlled securement and positioning of the elongate member 110 at the desired treatment site and/or position in the urethra 200.

The anchoring balloon 120 and adjustable locking device 10 further secure the energy delivery member 118 in the desired position or treatment site within the urethra 200 during the treatment of SUI, avoiding or minimizing displacement of the elongate member 110 relative to the treatment site. When the locking device 10 is engaged (i.e. locked) along a portion of the elongate member 100 and the inflated anchoring balloon 120 is disposed within the bladder 200 (as shown in FIG. 2), the anchoring balloon 120 resists, minimizes and/or avoid axial movement of the elongate member 110 and cuffing of the balloon, securing the desired position or treatment site of the SUI assembly 100. After the treatment of SUI is completed (i.e. desirable amount of energy delivered to the urethra 200 and/or to the parauretral region beyond the urethral wall), the anchoring balloon 120 is deflated, the cooling 122 balloon may or may not be deflated, and the locking device 10 may be disengaged and moved proximally along the elongate member 110, and the SUI assembly 100 is withdrawn from the treatment site.

Although, the use of the anchoring balloon 120 is described in connection with the assembly 100 for treatment of male and female SUI, it will be appreciated that the anchoring balloon 120 may be used in connection with any other type of assembly, device, catheter, tubular probe, shaft or any other configuration of an elongate member.

Figure 3A:
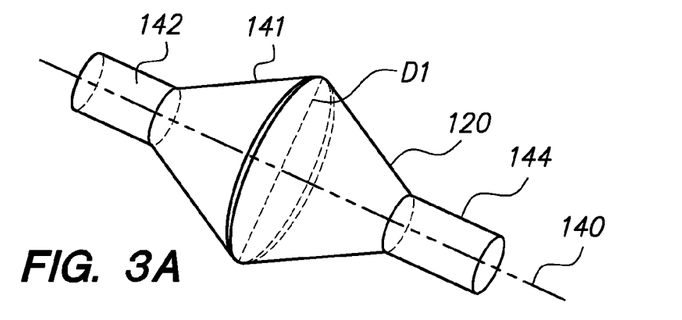
FIGS. 3A-E are perspective views of an anchoring balloon constructed according to various embodiments of the disclosed inventions.
Figure 3B:
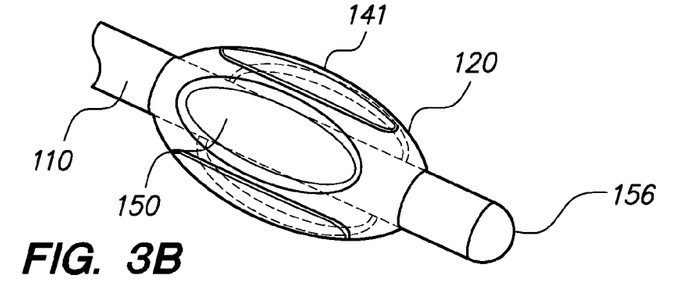
Figure 3C:
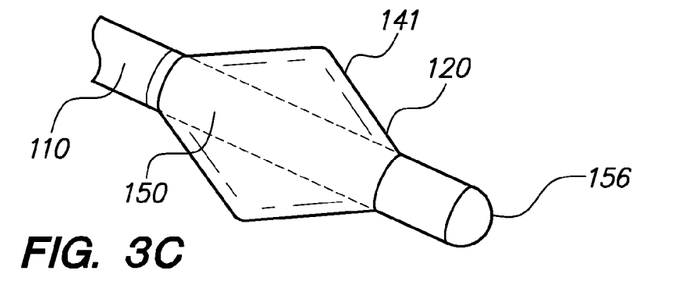
Figure 3D:
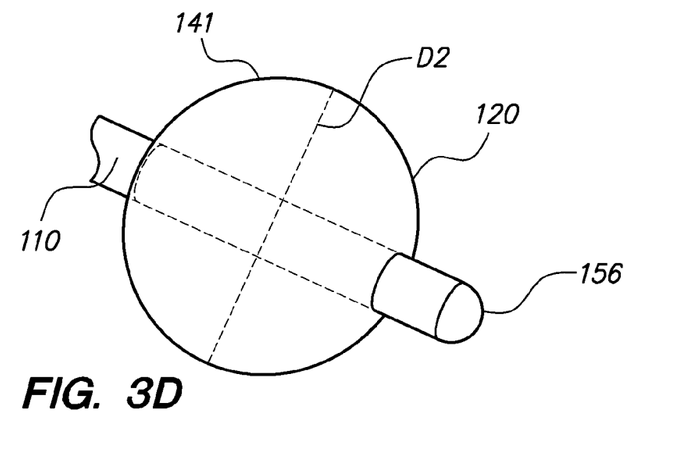
Figure 3E:
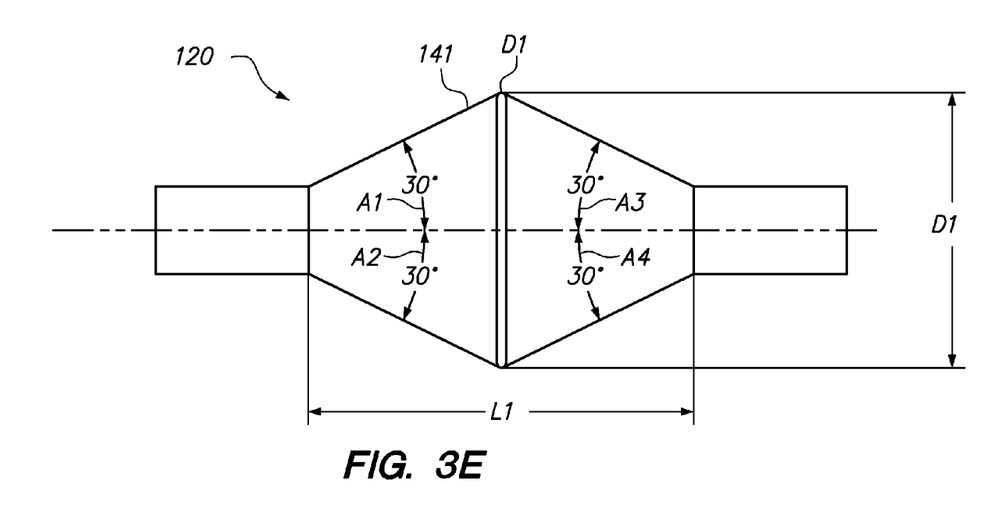
Figure 4:
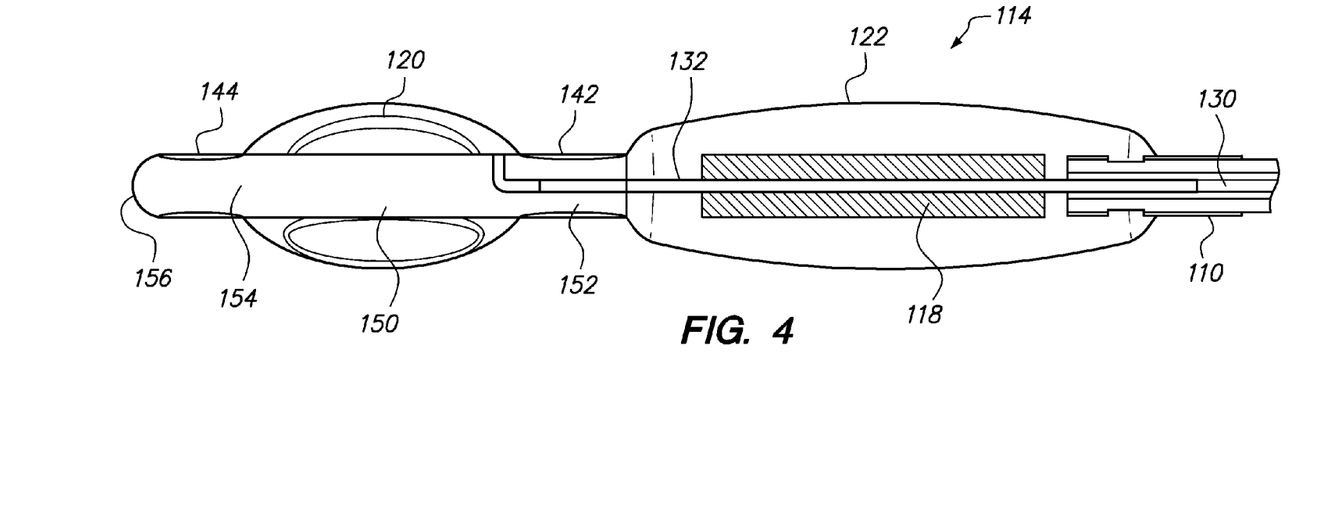
FIG. 4 is a cross-sectional view of an anchoring balloon coupled to the SUI assembly of FIG. 1, constructed according to one embodiment of the disclosed inventions.

FIGS. 3A-5B show various features of the anchoring balloon 120 according to embodiments of the inventions. The anchoring balloon 120 is shown in a preformed molded configuration (FIG. 3A), a pre-stretched or stretched-mounted (also deflated) configuration (FIG. 3B), and in an inflated or deployed configuration (FIGS. 3C-D). According to one embodiment of the invention, when supporting the anchoring balloon 120 to the SUI assembly 100, as shown in FIGS. 1 and 4, at least a portion of the elongate member 110 or other type of support structure (e.g. 150 of FIG. 4) is disposed within the balloon 120. Further, the support structure 150 engages and secures the anchoring balloon 120 in place, which will be discussed in greater detail below. The anchoring balloon 120 includes a first-end portion 142 (e.g. proximal), a middle-body portion 141 (e.g. expandable) and a second-end portion 144 (e.g. distal), collectively defining a sealed interior of the balloon through which the support structure 150, elongate member 110 or other type of elongate structure extends. As used in this specification, the term "support structure" may refer to any device or component to which one or more components may be directly or indirectly coupled, attached or secured. For example, the support structure 150 may include a plurality of elongate members (e.g. 132), where the first-end portion 142 of the balloon 120 is secured to a first elongate member of the support structure 150, and the second-end portion 144 of the balloon is secured to a second elongate member of the support structure 150. The first-end portion 142 and second-end portion 144 of the balloon 120 may include respective tubular or other suitable configurations to be coupled to the support structure 150 by adhesive, thermal bonding or the like, interlocking geometries, mechanical fastening, sutures or combinations thereof. The anchoring balloon 120 may be made of, or otherwise include polymeric materials, such as silicone, urethane polymer, thermoplastic elastomers rubber, such as santoprene, nylon, and polyethylene terephthalate (PET) and other suitable materials or combinations thereof. In one embodiment, the anchoring balloon 120 is composed of polyurethane which provides a balloon having superior performance and manufacturing attributes. Further, the anchoring balloon 120 material may have a shore durometer range between A90 to A100, and/or a shore durometer range between D30 to D70. For example, the anchoring balloon 120 may be manufactured with standard processing equipment to obtain a molded balloon having a wall thickness of approximately between 0.001 inches to 0.003 inches. Further, the wall thickness of the anchoring balloon 120 may vary from thicker, in and around the first-end portion 142 and in and around the second-end portion 144 to thinner in and around the a middle-body portion 141 at least. For example, the first-end portion 142 may have a wall thickness greater than a wall thickness of the middle-body portion 141.

In one embodiment of the invention and with the use of such standard molding procedures, a double conical or diamond molded configuration is manufactured (FIG. 3A). FIG. 3E illustrate an embodiment of the molded double conical or diamond configuration of the anchoring balloon 120, which may have an approximately angle of 30° (A1-4) from an axis 140 (e.g. aggregated 60°), a corresponding inside diameter D1 of approximately 13 millimeters (0.51 inches) at the center of the balloon 120, and a length L1 of approximately 18 millimeters (0.7 inches) at middle-body portion 141 of the balloon 120. By way of example, the anchoring balloon 120 can have a variety of shapes in the molded, mounted or inflated configurations, including but not limited to: a double conical, diamond, circular, oval, multi-sided, or irregular shapes, and/or angles that are adapted to resists or avoid cuffing of the balloon 120 when placed in-situ in a body cavity. Further, the balloon middle-body portion 141 has a non-tensioned length L1 (FIG. 3A, 3E), and the balloon middle-body portion 141 may be stretched to a tensioned length that is in a range of about 5% to about 35% greater than the non-tensioned length L1, and more preferably to a tensioned length that is in a range of about 8% to about 12% greater than the non-tensioned length L1 (FIG. 3B). When inflated (FIG. 3D), the anchoring balloon 120 may have a diameter D2 of approximately of 22 millimeters (0.86 inches).

The molded preformed configuration of the anchoring balloon 120, as shown in FIG. 3A, is stretched, for example, in a longitudinal direction along the axis 140 to form the pre-stretched or stretched-mounted configuration of the balloon 120, as shown in FIG. 3B. Further, the balloon 120 is stretch-mounted to the support structure 150 so as to be in tension relative to the support structure 150. Additionally, the balloon middle-body portion 141 may be twisted relative to the support structure 150.

In one embodiment, the balloon 120 is formed in a diamond-like configuration (FIG. 3A) that transitions to a substantially spherical configuration (FIG. 3D) when the balloon 120 is inflated to a inflation pressure that is at least about ten percent greater than atmospheric pressure external to the balloon 120, such that the balloon, when inflated to the inflation pressure and anchored in an anatomical body region, resists movement of the support structure 150 relative to the balloon 120.

As shown in FIGS. 3B and 4, the first and second end portions 142 and 144 of the balloon 120 may be secured to the elongate member 110 or suitable support structure using bonding, brazing, adhesive, thermal bonding or the like, interlocking geometries, mechanical fastening, sutures or combinations thereof. The molded configuration of the anchoring balloon 120 is stretched and the stretching of the balloon 120 is preferably in a longitudinal direction along the axis 140 of the molded configuration. In addition to the longitudinal stretch, the molded configuration of the anchoring balloon 120 may be rotated and/or twisted around the axis 140; rotation and/or twisting may occur simultaneously or consecutively with the longitudinal stretch of the anchoring balloon 120. As shown in FIG. 3C, an inflated configuration of the mounted anchoring balloon of FIG. 3B has a double conical or diamond configuration when the interior of the balloon is inflated to a pressure equal or similar to the atmospheric pressure. When the pressure of the interior of the balloon is higher than the atmospheric pressure (e.g. at least about ten percent greater than atmospheric pressure external to the balloon), the anchoring balloon 120 has a substantially spherical configuration when inflated, as shown in FIG. 3D. The inflated configurations of the anchoring balloon 120 (FIGS. 3C-D) resist or avoid cuffing of the balloon 120 when placed in-situ in a body cavity, further resisting movement of the elongate member 110 relative to the balloon. Alternatively, the inflated balloon 120 may have an elliptical or other suitable inflated configuration when the molded anchoring balloon has other shapes including but not limited to: a circular, oval, multi-sided, or irregular shapes.

FIG. 4 illustrates the anchoring balloon 120 in an unexpanded, pre-stretched or stretched-mounted configuration disposed on the distal portion 114 of the SUI assembly 100 according to one embodiment of the disclosed inventions. The elongate member 110 includes at least a lumen 130 that accommodates a hypotube 132 within the cooling balloon 122 and energy delivery member 118, and provides a fluid path for inflation and deflation of the anchoring balloon 120. The structure of the assembly 100 and elongate member 110 allows fluid communication between a fluid port 134 (FIG. 1), the lumen 130 (FIG. 4) and the anchoring balloon 120. A seal 136 (FIG. 1) is included at the fluid port 134 to provide a fluid seal and maintain inflation or deflation of the anchoring balloon 120. Alternatively, the fluid seal may be positioned at any suitable location between the fluid port 134 and the anchoring balloon 120. An inflation source (not shown) is fluidly connected to the lumen 130 to deliver and/or withdraw fluid from the anchoring balloon 120. From the proximal opening of the lumen 130 at the fluid port 134, the introduced fluid travels in the lumen 130 into the interior of the balloon 120 to inflate the balloon thereof.

Further, the distal portion 114 of the assembly 100 may include a support structure 150 where the stretched configuration of the anchoring balloon 120 is mounted. The support structure 150 may be composed of rigid, semi-rigid and/or compliant materials and/or alloys, such as, acrylonitrile butadiene styrene (ABS), or combination thereof. The support structure 150 includes a first location 152 (e.g. proximal portion) and a second location 154 (e.g. distal portion). The first location 152 of the support structure 150 secures the first-end portion 142 of the anchoring balloon 120, while the second location 154 of the support structure secures the second-end portion 144 of the anchoring balloon 120, using bonding, brazing, adhesive, thermal bonding or the like, interlocking geometries, mechanical fastening, sutures or combinations thereof. For example, the first-end portion 142 of the balloon is secured to the support structure 150 at the first location 152, and the second-end portion 144 is secured to the support structure 150 at the second location 154 distal to the first location 152, and to the middle-body portion 141. The first location 152 of the support structure 150 may accommodate a portion of the hypotube 132 to provide fluid communication of the lumen 130 to the anchoring balloon 120. The second location 154 of the support structure 150 may include a non-traumatic, semi-spherical or rounded tip end 156. Further, the anchoring balloon 120 is stretch-mounted to the support structure 150 so as to be in tension relative to the support structure 150. In one embodiment, the balloon 120 is formed in a diamond-like configuration (FIG. 3A) that transitions to a substantially spherical configuration (FIG. 3A) when the balloon 120 is inflated to a inflation pressure that is at least about ten percent greater than atmospheric pressure external to the balloon 120, such that the balloon, when inflated to the inflation pressure and anchored in an anatomical body region, resists movement of the support structure 150 relative to the balloon 120.

Figure 5A:
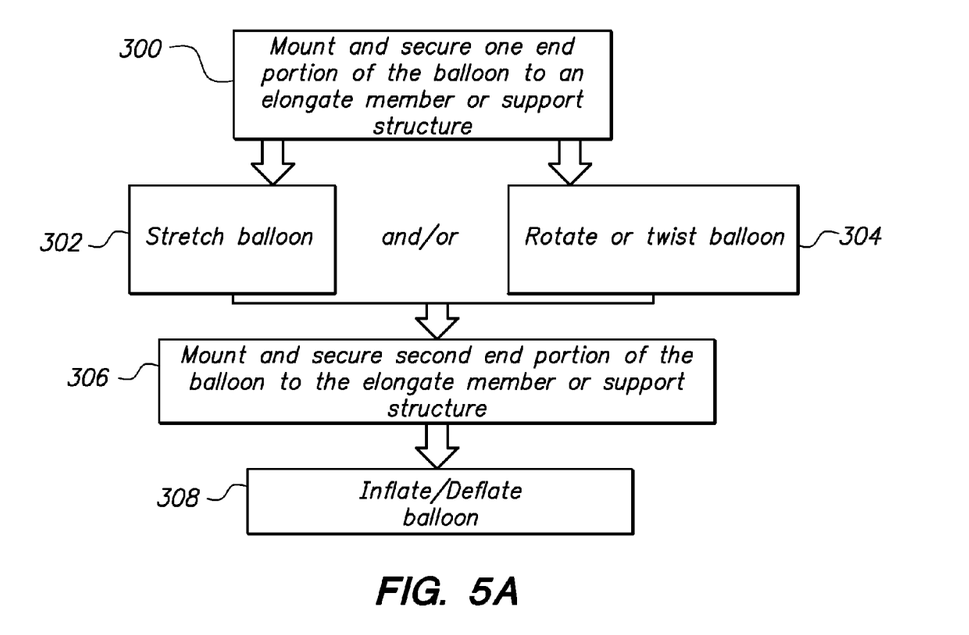
FIGS. 5A-B are flow charts showing methods of manufacturing an anchoring balloon according to one embodiment of the disclosed inventions.

As shown in FIG. 5A, the anchoring balloon 120 may be manufactured by forming an inflatable balloon 120 having a first-end portion 142, a second-end portion 144, and a middle-body portion 141, the middle-body portion 141 having a first end integrally formed with or otherwise bonded to the first-end portion, and a second end integrally formed with or otherwise bonded to the second-end portion, the first-end portion having a wall thickness greater than a wall thickness of the middle-body portion 141. Then, securing the first-end portion 142 to the first location 152 on an elongate support structure 150 (step 300). Securing the second-end portion 144 of the balloon 120 to a second location 154 (step 306) distal to the first location 152 on the elongate support structure 150, the first and second locations being spaced apart such that the balloon 120 is stretch-mounted (step 302) to the support structure 150 so as to be in tension relative to the support structure 150, where the first-end portion 142, middle-body portion 141 and second-end portion 144 of the balloon 120 collectively define a sealed interior of the balloon 120 through which the support structure 150 extends. The balloon 120 is formed in a diamond-like configuration that transitions to a substantially spherical configuration when the balloon 120 is inflated to an inflation pressure that is at least about ten percent greater than atmospheric pressure external to the balloon 120.

In addition to the stretch-mounting step, the middle-body portion 141 of the balloon 120 is twisted (step 304) relative to the support structure 150 prior to securing the second-end portion 144 of the balloon 120 to the support structure 150. The support structure 150 may include a plurality of elongate members, where the first-end portion 142 of the balloon 120 is secured to a first elongate member of the support structure 150, and the second-end portion 144 of the balloon is secured to a second elongate member of the support structure 150. Further, the first-end portion 142 and second-end portion 144 of the balloon 120 are each secured to the support structure 150 by one of adhesive bonding, thermal bonding, interlocking geometries, and mechanical fastening.

In one embodiment, the mounted balloon 120 is manufactured by securing one end portion of the balloon 120 (either the first-end portion 142 or the second-end portion 144 portion) to the support structure 150 (step 300), then balloon 120 is stretched (step 302), and then, the unsecured end portion of the balloon 120 is also secured to support structure 150 (step 306). In addition to the stretching, the anchoring balloon 120 may be rotated and/or twisted around the axis 140 (step 304) simultaneously or consecutively with the longitudinal stretching of the balloon 120. After stretching, rotation and/or twisting of anchoring balloon 120, the unsecured second end portion of the balloon 120 is mounted and secured to the support structure 150 (step 306). Subsequent to the securement of the first-end portion 142 and second-end portion 144 end portions after stretching, rotation and/or twisting of the balloon 120, the pre-stretched or stretched-mounted configuration of the balloon 120 is formed, as shown in FIG. 3B. Then, the balloon 120 may be deflated, as shown in FIG. 3B, and/or inflated, as shown in FIGS. 3C-D (step 308).

Figure 5B:
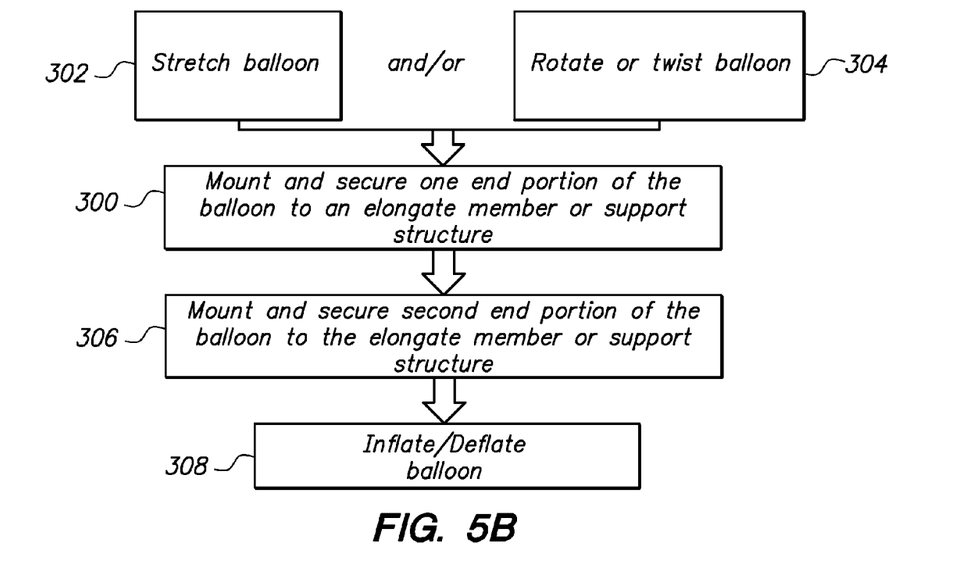

Alternatively, as shown in FIG. 5B, the anchoring balloon 120 may be manufactured by first stretching the molded configuration of the anchoring balloon 120 (step 302) along the axis 140, before mounting the anchoring balloon 120 to the support structure 150. In addition to the stretching, the anchoring balloon 120 may be rotated and/or twisted around the axis 140 (step 304) simultaneously or consecutively with the longitudinal stretching of the balloon 120. Next, one end portion of the balloon 120 (i.e. either the first-end portion 142 or the second-end portion 144 portion) is mounted and secure to the support structure 150 (step 300). Then, the second end portion of the balloon 120 is also mounted and secured to the elongate member 110 or support structure 150 (step 306).

Experimental Data

Figure 6A:
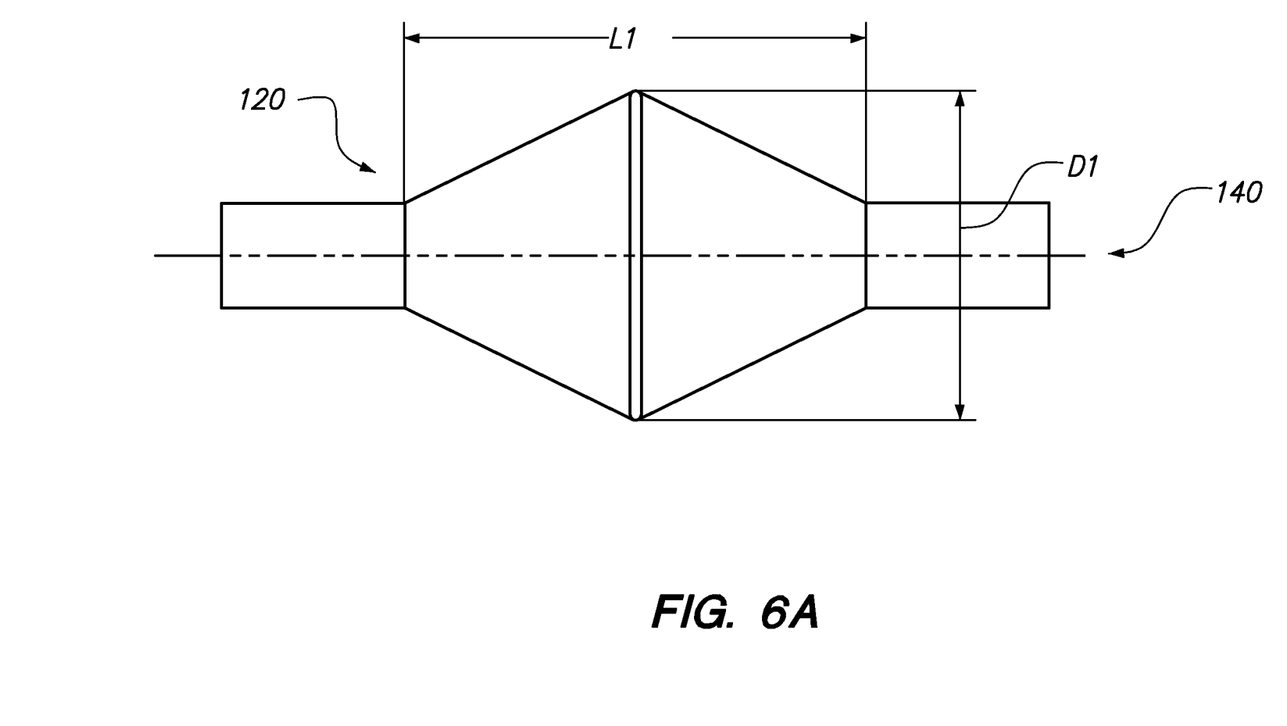
FIGS. 6A-B are cross-sectional view of the anchoring balloon of FIG. 3A, and experimental data table according to embodiments of the invention.
Figure 6B:
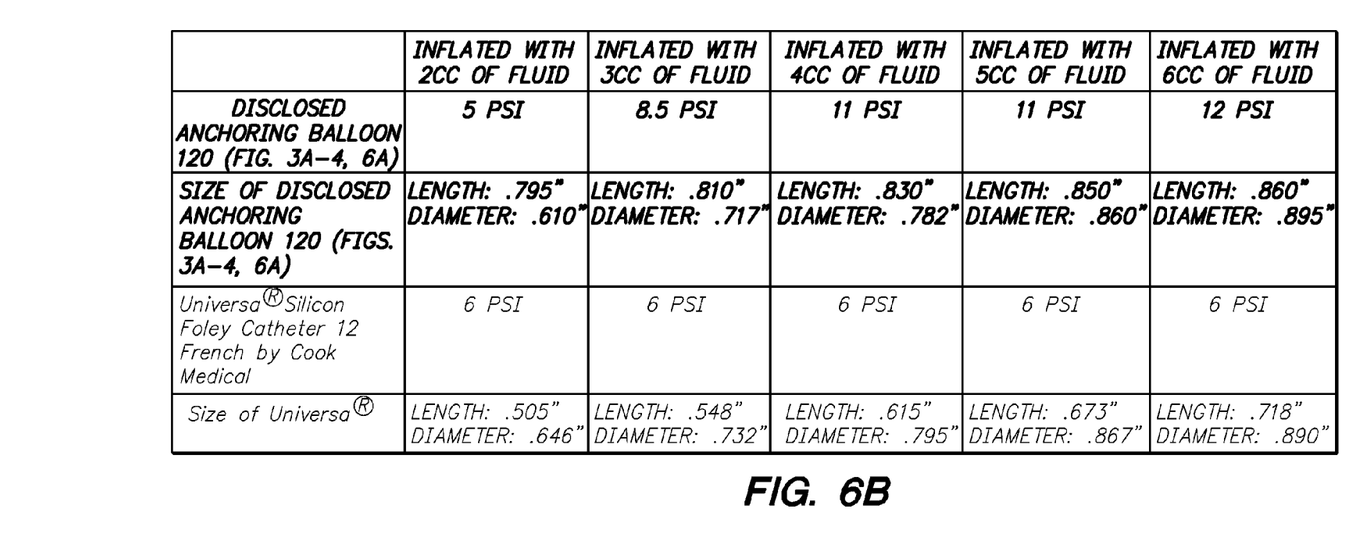
Figure 7:
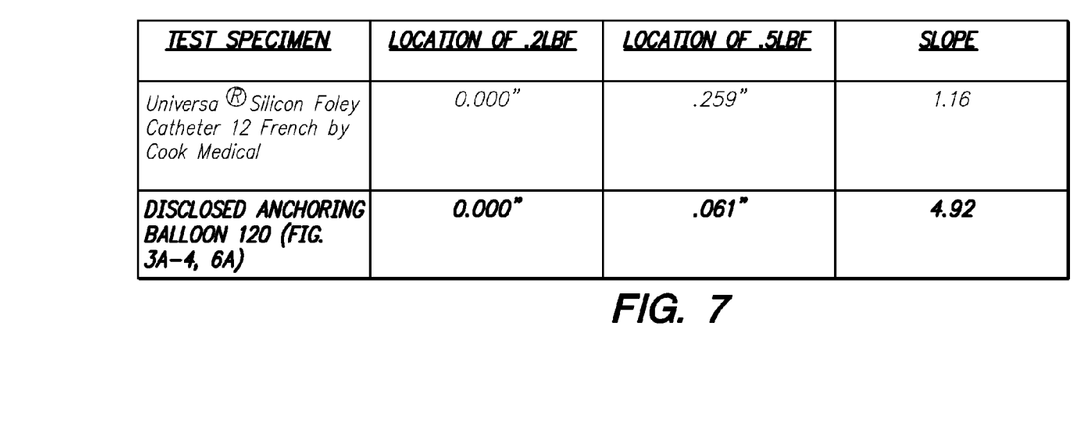
FIG. 7 is an experimental data table according to embodiments of the invention.

In accordance with the disclosed inventions, experiments were conducted on a pre-stretched or stretched-mounted anchoring balloon 120 of a molded configuration having a diameter D1 and a length L1, as shown in FIG. 6A. The results from the pressure tests and dimensional analysis (diameter and length variations) on the anchoring balloon 120 (FIGS. 3A-4 and 6A) when inflated by fluid and/or gas at ambient room conditions are shown in FIG. 6B in comparison with a Silicon Foley Catheter 12 French (Universa® by Cook Medical).

In accordance with the disclosed inventions, FIG. 7 illustrates experimental data conducted on the anchoring balloon 120 (FIGS. 3A-4 and 6A) when being placed through the urethra 200 into the bladder 220 (as shown in FIG. 2). The results are shown in comparison with a Silicon Foley Catheter 12 French (Universa® by Cook Medical). The anchoring balloon 120 constructed according to the embodiments of the disclosed invention is configured to provide a substantially immediate and sharp rise in tactile feedback to the end user or physician, particularly under low force or load conditions (e.g. represented as the slope of force over displacement in FIG. 7) to detect location of the anchoring balloon 120 within the bladder 220. The slope column of FIG. 7 represents the amount of force (e.g. applied by physician/user to the balloon when pulling or withdrawing the medical assembly in-situ), over the displacement (e.g. distance to balloon moves over that force range).

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A medical device, comprising:
   an elongate support structure; and
   an inflatable balloon, the balloon comprising a first-end portion secured to the support structure at a first location, a second-end portion secured to the support structure at a second location distal to the first location, and a middle-body portion,
   the middle-body portion having a first end integrally formed with or otherwise bonded to the first-end portion, and a second end integrally formed with or otherwise bonded to the second-end portion,
   the first-end portion having a wall thickness greater than a wall thickness of the middle-body portion,
   the respective first-end portion, middle-body portion and second-end portion collectively defining a sealed interior of the balloon through which the support structure extends,
   the balloon being stretch-mounted to the support structure so as to be in tension relative to the support structure,
   wherein the balloon is formed in a diamond shaped configuration that transitions to a substantially spherical configuration when the balloon is inflated to an inflation pressure that is at least about ten percent greater than atmospheric pressure external to the balloon,
   such that the balloon, when inflated to the inflation pressure and anchored in an anatomical body region, resists movement of the support structure relative to the balloon.

2. The medical device of claim 1, wherein the balloon middle-body portion is twisted relative to the support structure.

3. The medical device of claim 1, wherein the support structure comprises a plurality of elongate members, and wherein the first-end portion of the balloon is secured to a first elongate member of the support structure, and the second-end portion of the balloon is secured to a second elongate member of the support structure.

4. The medical device of claim 1, wherein the first-end portion and second-end portion of the balloon are each secured to the support structure by one of adhesive bonding, thermal bonding, interlocking geometries, and mechanical fastening.

5. The medical device of claim 1, wherein the balloon comprises one or more polymeric materials.

6. The medical device of claim 5, wherein the balloon comprises a shore durometer in a range of between about A90 to about A100.

7. The medical device of claim 5, wherein the balloon comprises a shore durometer in a range of between about D30 to about D70.

8. The medical device of claim 1, wherein the balloon, when inflated to the inflation pressure, resists cuffing relative to the support structure.

9. The medical device of claim 1, wherein the inflation pressure is at least about 12 percent greater than the atmospheric pressure.

10. The medical device of claim 1, wherein the balloon middle-body portion has a non-tensioned length, and wherein the balloon middle-body portion is stretched to a tensioned length that is in a range of about 8% to about 12% greater than the non-tensioned length.

11. A method of manufacturing a medical device, comprising:
   forming an inflatable balloon having a first-end portion, a second-end portion, and a middle-body portion, the middle-body portion having a first end integrally formed with or otherwise bonded to the first-end portion, and a second end integrally formed with or otherwise bonded to the second-end portion, the first-end portion having a wall thickness greater than a wall thickness of the middle-body portion;
   securing the first-end portion of the balloon to a first location on an elongate support structure; and
   securing the second-end portion of the balloon to a second location distal to the first location on the elongate support structure, the first and second locations being spaced apart such that the balloon is stretch-mounted to the support structure so as to be in tension relative to the support structure, the first-end portion, middle-body portion and second-end portion of the balloon collectively define a sealed interior of the balloon through which the support structure extends,
   wherein the balloon is formed in a diamond shaped configuration that transitions to a substantially spherical configuration when the balloon is inflated to an inflation pressure that is at least about ten percent greater than atmospheric pressure external to the balloon.

12. The method of claim 11, wherein the middle-body portion of the balloon is twisted relative to the support structure prior to securing the second-end portion of the balloon to the support structure.

13. The method of claim 11, wherein the support structure comprises a plurality of elongate members, and wherein the first-end portion of the balloon is secured to a first elongate member of the support structure, and the second-end portion of the balloon is secured to a second elongate member of the support structure.

14. The method of claim 11, wherein the first-end portion and second-end portion of the balloon are each secured to the support structure by one of adhesive bonding, thermal bonding, interlocking geometries, and mechanical fastening.

15. The method of claim 11, wherein the balloon comprises one or more polymeric materials.

16. The method of claim 15, wherein the balloon comprises a shore durometer in a range of between about A90 to about A100.

17. The method of claim 15, wherein the balloon comprises a shore durometer in a range of between about D30 to about D70.

18. The method of claim 11, wherein the balloon middle-body portion has a non-tensioned length, and wherein the balloon middle-body portion is stretched to a tensioned length that is in a range of about 8% to about 12% greater than the non-tensioned length.

* * * * *